United States Patent
Kielhorn et al.

(10) Patent No.: US 10,302,568 B2
(45) Date of Patent: May 28, 2019

(54) CELL COUNTER

(71) Applicant: DeNovix, Inc., Wilmington, DE (US)

(72) Inventors: Fernando F. Kielhorn, Wilmington, DE (US); Daniel A. Schieffer, Philadelphia, PA (US); David L. Ash, Hockessin, DE (US); Kevin Kelley, Mickleton, NJ (US)

(73) Assignee: Denovix, Inc., Wilmington, DE (US)

( * ) Notice: Subject to any disclaimer, the term of this patent is extended or adjusted under 35 U.S.C. 154(b) by 149 days.

(21) Appl. No.: 15/628,394

(22) Filed: Jun. 20, 2017

(65) Prior Publication Data

US 2017/0370848 A1    Dec. 28, 2017

Related U.S. Application Data

(60) Provisional application No. 62/353,226, filed on Jun. 22, 2016, provisional application No. 62/489,181, filed on Apr. 24, 2017.

(51) Int. Cl.
*G01N 21/64* (2006.01)
*G01N 21/03* (2006.01)
(Continued)

(52) U.S. Cl.
CPC ..... *G01N 21/6458* (2013.01); *G01N 15/1434* (2013.01); *G01N 15/1468* (2013.01);
(Continued)

(58) Field of Classification Search
CPC ............... G01N 15/14; G01N 15/1434; G01N 15/1468; G01N 2015/144; G01N 2015/1481; G01N 2021/035; G01N 21/6456; G01N 21/6458; G01N 2201/062; G01N 33/487; G02B 21/06; G06K 9/00127; G06M 11/02; C12Q 1/06; C12M 1/34
(Continued)

(56) References Cited

U.S. PATENT DOCUMENTS 6,870,165 B2    3/2005    Amirkhanian et al.
7,990,525 B2    8/2011    Kanda
(Continued)

FOREIGN PATENT DOCUMENTS

EP    1 950 553 A1    7/2008

OTHER PUBLICATIONS

International Search Report and Written Opinion in International Application No. PCT/US2017/038328, dated Sep. 22, 2017.

*Primary Examiner* — Maureen Wallenhorst
(74) *Attorney, Agent, or Firm* — Potter Anderson and Corroon LLP

(57) ABSTRACT

Cell counters and methods of their use are disclosed herein. The cell counters comprise a sample mounting system that includes a base comprising a mounted lower sample surface and a cover comprising a mounted upper sample surface; a bright-field light source incorporated in the cover; an objective lens mounted below the sample mounting system; optionally, a fluorescence excitation source in optical communication with the sample mounting system; and an imaging system in optical communication with the bright-field light source and the objective lens. The mounted sample surfaces are configured for repeated use, such that disposable sample cartridges are not needed.

21 Claims, 7 Drawing Sheets

(51) Int. Cl.
    *G01N 15/14*      (2006.01)
    *G01N 33/487*     (2006.01)
    *G02B 21/06*      (2006.01)
    *G06M 11/02*      (2006.01)
    *C12M 1/34*       (2006.01)
    *C12Q 1/06*       (2006.01)
    *G06K 9/00*       (2006.01)

(52) U.S. Cl.
    CPC ....... *G01N 21/6456* (2013.01); *G01N 33/487* (2013.01); *G02B 21/06* (2013.01); *G06K 9/00127* (2013.01); *C12M 1/34* (2013.01); *C12Q 1/06* (2013.01); *G01N 15/14* (2013.01); *G01N 2015/144* (2013.01); *G01N 2015/1481* (2013.01); *G01N 2021/035* (2013.01); *G01N 2201/062* (2013.01); *G06M 11/02* (2013.01)

(58) Field of Classification Search
    USPC ...... 436/43, 46, 63, 164, 165, 172; 359/387; 422/68.1, 73, 82.05, 82.08, 82.09; 435/4, 435/29, 39, 325, 366, 288.7
    See application file for complete search history.

(56)               References Cited

U.S. PATENT DOCUMENTS

| | | |
|---|---|---|
| 8,883,491 B2 | 11/2014 | Lin et al. |
| 9,046,489 B2 | 6/2015 | Lim et al. |
| 2010/0085568 A1 | 4/2010 | Robertson, Jr. et al. |
| 2013/0099120 A1* | 4/2013 | Chan .................. G01N 15/1463 250/338.1 |
| 2014/0291547 A1 | 10/2014 | Lim et al. |
| 2015/0233760 A1 | 8/2015 | Kielhorn et al. |

\* cited by examiner

CELL COUNTER

FIELD

This disclosure relates to a cell counter comprising bright-field and fluorescence imaging modes, with the cell counter utilizing a sample mounting system that does not rely on disposable cartridges.

BACKGROUND

In many medical and biological fields, cell counting is a critical aspect of laboratory analysis. Cells can be counted manually, for example by simple counts on slides or in a counting chamber, or automatically using, for example, flow cytometry or image analysis. It is this last area, image analysis, that has gained in usage in recent years, given the flexibility in image analysis systems and the relative low cost as compared to typical flow cytometers.

Image analysis systems utilize both transmitted light and fluorescence to produce static images of viable and/or dead cells in a sample. Optics usually comprise an objective lens in optical communication with a detection system, typically a charge-coupled device (CCD) camera or a complementary metal-oxide-semiconductor (CMOS) camera. Images produced by the camera are then transmitted to a computer for analysis by software designed to count cells in the bright-field or fluorescence images or alone or in combination.

U.S. Pat. Nos. 8,883,491 and 9,046,489 disclose cell counters that utilize the combination of bright-field light and fluorescent light for cell counting. In U.S. Pat. No. 8,883,491; a cell counting system takes images of a static population of cells in a sample that has been loaded into a chamber having a fixed height. Because the system utilizes a covered chamber having a fixed height, cell concentration can be determined from the cell count. U.S. Pat. No. 9,046,489 discloses a fluorescence imaging device that comprises a fluorescence light source, a light source configured to emit white light or monochromatic light, an excitation filter, a dichroic mirror configured to transmit excitation light transmitted by the excitation filter and reflect light fluorescence emission light, an objective lens, an emission filter configured to transmit fluorescence emission light of a predetermined wavelength, and a detector.

A significant disadvantage of automated image analysis systems described above is their use of cartridges for sample analysis. Similar to the so-called "razor blade model" (except without the initial low cost purchase of the base item), these cartridges are single use, disposable items that lead to high costs for the user. Further, these cartridges tend to be designed for specific devices, and cannot be used with cell counters from other manufacturers or even other devices from the same manufacturer.

A fixed path length over a defined surface area establishes a fixed sample volume for analysis. The cell density of the sample may be too low or too high for accurate cell counting thereby limiting the effective detection range of the apparatus. Additionally cells can clump on top of each other in a fixed path length chamber excluding the cells that are out of the field of focus from being counted.

Reducing the path length to less than twice the diameter of the cell will force all cells in a sample into the same focal plane.

Thus, there remains a need for cell counters and methods of use thereof that reduce cost, provide greater analysis flexibility, and improve data quality.

SUMMARY

One aspect of the disclosure features a cell counter comprising: (i) a bright-field light source; (ii) optionally, a fluorescence excitation source; (iii) an imaging system; and (iv) a sample mounting system comprising: (A) a base having a base top side, a base bottom side, an adjustment pin hole through the base top side to the base bottom side configured to receive a height adjustment pin, and an objective lens cavity positioned near a proximal end of the base bottom side configured to align with an objective lens of the imaging system; (B) a hinge fixed to the base in a position distal to the objective lens cavity; (C) a movable arm fixed to the hinge, said movable arm having a movable arm top side, a movable arm bottom side, a height adjustment pin receiver fixed to the movable arm bottom side in a position aligned with the adjustment pin hole when the movable arm is in a closed position, and a bright-field light source cavity near a proximal end of the movable arm configured to receive the bright-field light source; (D) a lower sample surface mounted to the base top side in a position configured to receive bright-field light from the bright-field light source when the movable arm is in the closed position and to receive fluorescent light from the fluorescence excitation source (when present); (E) an upper sample surface mounted to the movable arm bottom side of the movable arm in a position configured to receive fluorescent light from the fluorescence excitation source (when present) when the movable arm is in the closed position and to receive bright-field light from the bright field light source; and (F) a height adjustment pin mounted to the base through the adjustment pin hole.

In certain embodiments, the above-described cell counter comprises a fluorescence excitation source, wherein the lower sample surface is configured to receive fluorescent light from the fluorescence excitation source and/or the upper sample surface is configured to receive fluorescent light from the fluorescence excitation source when the movable arm is in the closed position. In particular, the objective lens cavity is further configured to align with the fluorescence excitation source, with more particular embodiments comprising an imaging system that includes the objective lens, a dichroic mirror and an emission filter. In such embodiments, the dichroic mirror can be configure to reflect fluorescence excitation light and transmit fluorescence emission light, or the dichroic mirror can be configured to transmit fluorescence excitation light and reflect fluorescence emission light.

In various embodiments of the above-described cell counter, the height adjustment pin is connected to an actuator. In certain embodiments, the height adjustment pin is a precision screw and the actuator is a motor.

In various embodiments, the movable arm further comprises a calibrator (also referred to herein as a "calibration means") for detecting and/or calibrating the distance between the lower sample surface and the upper sample surface, either directly or indirectly, e.g., via measuring distance between the base and the movable arm at a predetermined location. For instance, the calibrator can comprise a distance sensor disposed in one or both of the base and the movable arm.

In certain embodiments, the sample mounting system comprises a detector for detecting contact between the height adjustment pin and the height adjustment pin receiver. In particular embodiments, the detector accomplishes this by detecting completion of an electrical circuit formed by the contact between the height adjustment pin and the height adjustment pin receiver. In certain embodiments, contact between the height adjustment pin and the height adjustment pin receiver is made when the upper sample surface is in direct contact with the lower sample surface in the absence of a sample.

A second aspect disclosed herein features a method of counting cells comprising: (a) providing a cell counter of the type described above, (b) loading a sample onto the lower sample surface of the cell counter; (c) before, after, or simultaneously with step (b), moving the movable arm to a closed position relative to the base; (d) illuminating the sample via the bright-field light source, the fluorescence excitation source (when present), or a combination thereof (when the fluorescence excitation source is present); and (e) detecting and counting cells via the imaging system to produce cell count data. The method can further comprise, after step (c) the step of adjusting a distance between the base and the movable arm via the height adjustment pin.

In various embodiments, the step of moving the movable arm and/or adjusting the distance between the base and the movable arm is/are automated.

The method can also comprise the further steps of: (f) adjusting the amount of sample on the lower sample surface based on the cell count data; and (g) repeating steps (d) and (e).

In certain embodiments, the above described method comprises setting a zero gap measurement, which is a measurement set when the lower sample surface and the upper sample surface are in direct contact in the absence of a sample. In one embodiment, this is done by (1) placing the upper sample surface in direct contact with the lower sample surface in the absence of a sample, (2) moving the height adjustment pin into contact with the height adjustment pin receiver, and (3) detecting the contact between the height adjustment pin and the height adjustment pin receiver when the upper sample surface is in direct contact with the lower sample surface in the absence of a sample. In particular embodiments, the contact between the height adjustment pin and the height adjustment pin receiver completes a circuit and the detection comprises detecting the completion of the circuit. Alternatively, the contact between the height adjustment pin and the height adjustment pin receiver can be detected by a distance sensor.

A third aspect features a cell counter comprising: (i) a sample mounting system comprising: (A) a base comprising a mounted lower sample surface; and (B) a cover comprising a mounted upper sample surface; (ii) a bright-field light source incorporated in the cover; (iii) an objective lens mounted below the sample mounting system; (iv) a dichroic mirror in optical communication with the bright-field light source and the objective lens; (v) a fluorescence excitation source in optical communication with the dichroic mirror; and (vi) an imaging system in optical communication with the bright-field light source, the objective lens, and the dichroic mirror.

In certain embodiments, the sample mounting system comprises a calibrator for detecting and/or calibrating the distance between the lower sample surface and the upper sample surface, either directly or indirectly, e.g., via measuring distance between the base and the movable arm at a pre-determined location. For instance, the calibrator can comprise a distance sensor disposed in one or both of the base and the cover.

In certain embodiments of this cell counter, the sample mounting system comprises a height adjustment pin in one of the base or the cover. This embodiment of sample mounting system can also include a height adjustment pin receiver in the other of the base or the cover. The height adjustment pin can be connected to an actuator. In one embodiment, the height adjustment pin is a precision screw and the actuator is a motor.

In various embodiments wherein the base of the cell counter is connected to the cover via a hinge.

In certain embodiments of the above-described cell counter comprising a height adjustment pin and a height adjustment pin receiver, the cell counter also comprises a detector for detecting contact between the height adjustment pin and the height adjustment pin receiver. In particular embodiments, the detector accomplishes this by detecting completion of an electrical circuit formed by the contact between the height adjustment pin and the height adjustment pin receiver. In certain embodiments, contact between the height adjustment pin and the height adjustment pin receiver is made when the upper sample surface is in direct contact with the lower sample surface in the absence of a sample.

A fourth aspect features a method of counting cells comprising: (a) providing a cell counter as described in the third aspect above; (b) loading a sample onto the mounted lower sample surface of the cell counter; (c) before, after, or simultaneously with step (b), moving the cover to a closed position relative to the base; (d) illuminating the sample via the bright-field light source, the fluorescence excitation source, or a combination thereof; and (e) detecting and counting cells via the imaging system to produce cell count data. The method can further comprise, after step (c) the step of adjusting a distance between the base and the movable arm via the height adjustment pin.

In various embodiments, the step of moving the movable arm and/or adjusting the distance between the base and the movable arm is/are automated.

The method can also comprise the further steps of: (f) adjusting the amount of sample on the lower sample surface based on the cell count data; and (g) repeating steps (d) and (e).

In certain embodiments, the method comprises setting a zero gap measurement by determining the distance between a point on the cover and a point on the base when the upper sample surface and the lower sample surface are in direct contact. In particular embodiments wherein the cell counter includes a height adjustment pin and a height adjustment pin receiver, this can be accomplished by (1) placing the upper sample surface in direct contact with the lower sample surface in the absence of a sample, (2) moving the height adjustment pin into contact with the height adjustment pin receiver, and (3) detecting the contact between the height adjustment pin and the height adjustment pin receiver when the upper sample surface is in direct contact with the lower sample surface in the absence of a sample. In particular embodiments, the contact between the height adjustment pin and the height adjustment pin receiver completes a circuit and the detection comprises detecting the completion of the circuit. Alternatively, the contact between the height adjustment pin and the height adjustment pin receiver can be detected by a distance sensor.

A fifth aspect disclosed herein features a cell counter comprising: (i) a sample mounting system comprising: (A) a base comprising a mounted lower sample surface; and (B) a cover comprising a mounted upper sample surface; (ii) a bright-field light source incorporated in the cover; (iii) an objective lens mounted below the sample mounting system; (iv) optionally, a fluorescence excitation source; and (v) an imaging system in optical communication with the bright-field light source and the objective lens.

In certain embodiments, the sample mounting system comprises a calibrator for detecting and/or calibrating the distance between the lower sample surface and the upper sample surface, either directly or indirectly, e.g., via measuring distance between the base and the cover at a pre-determined location. For instance, the calibrator can comprise a distance sensor disposed in one or both of the base and the cover. In certain embodiments of this cell counter, the sample mounting system comprises a height adjustment pin in one of the base or cover. In this embodiment, the sample mounting system can also include a height adjustment pin receiver in the other of the base or cover. The height adjustment pin can be connected to an actuator. In one embodiment, the height adjustment pin is a precision screw and the actuator is a motor.

In various embodiments wherein the base of the cell counter is connected to the cover via a hinge.

In embodiments of the above-described cell counter comprising a height adjustment pin and a height adjustment pin receiver, the cell counter also comprises a detector for detecting contact between the height adjustment pin and the height adjustment pin receiver. In particular embodiments, the detector accomplishes this by detecting completion of an electrical circuit formed by the contact between the height adjustment pin and the height adjustment pin receiver. In certain embodiments, contact between the height adjustment pin and the height adjustment pin receiver is made when the upper sample surface is in direct contact with the lower sample surface in the absence of a sample.

A sixth aspect features a method of counting cells comprising: (a) providing a cell counter as described in the fifth aspect above; (b) loading a sample onto the mounted lower sample surface of the cell counter; (c) before, after, or simultaneously with step (b), moving the cover to a closed position relative to the base; (d) illuminating the sample via the bright-field light source, the fluorescence excitation source (when present), or a combination thereof (when the fluorescence excitation source is present); and (e) detecting and counting cells via the imaging system. The method can further comprise, after step (c) the step of adjusting a distance between the base and the movable arm via the height adjustment pin.

In various embodiments, the step of moving the movable arm and/or adjusting the distance between the base and the movable arm is/are automated.

The method can also comprise the further steps of: (f) adjusting the amount of sample on the lower sample surface based on the cell count data; and (g) repeating steps (d) and (e).

In certain embodiments, the method comprises setting a zero gap measurement by determining the distance between a point on the cover and a point on the base when the upper sample surface and the lower sample surface are in direct contact. In particular embodiments wherein the cell counter includes a height adjustment pin and a height adjustment pin receiver, this can be accomplished by (1) placing the upper sample surface in direct contact with the lower sample surface in the absence of a sample, (2) moving the height adjustment pin into contact with the height adjustment pin receiver, and (3) detecting the contact between the height adjustment pin and the height adjustment pin receiver when the upper sample surface is in direct contact with the lower sample surface in the absence of a sample. In particular embodiments, the contact between the height adjustment pin and the height adjustment pin receiver completes a circuit and the detection comprises detecting the completion of the circuit. Alternatively, the contact between the height adjustment pin and the height adjustment pin receiver can be detected by a distance sensor.

A seventh aspect of the disclosure features a cell counter comprising: (i) a bright-field light source; (ii) an imaging system; (iii) optionally, a fluorescence excitation source; and (iv) a sample mounting system comprising: (A) a base having a base top side, a base bottom side, and an objective lens cavity configured to align with an objective lens of the imaging system; (B) a hinge fixed to the base; (C) a movable arm fixed to the hinge, said movable arm having a movable arm top side, a movable arm bottom side, and a bright-field light source cavity near a proximal end of the movable arm configured to receive the bright-field light source; (D) a lower sample surface mounted to the base top side in a position configured to receive bright-field light from the bright-field light source when the movable arm is in the closed position and to receive fluorescent light from the fluorescence excitation source (when present); and (E) an upper sample surface mounted to the movable arm bottom side of the movable arm in a position configured to receive fluorescent light from the fluorescence excitation source (when present) when the movable arm is in the closed position and to receive bright-field light from the bright field light source.

The above-described cell counter can comprise a fluorescence excitation source in which the lower sample surface is configured to receive to receive fluorescent light from the fluorescence excitation source and/or the upper sample surface is configured to receive fluorescent light from the fluorescence excitation source when the movable arm is in the closed position. In certain embodiments, the objective lens cavity is configured to receive the fluorescence excitation source.

In certain embodiments, the imaging system comprises the objective lens; a dichroic mirror; and an emission filter. The dichroic mirror can be configured to reflect fluorescence excitation light and transmit fluorescence emission light, or it can be configured to transmit fluorescence excitation light and reflect fluorescence emission light.

In certain embodiments, the sample mounting system comprises a calibrator for detecting and/or calibrating the distance between the lower sample surface and the upper sample surface, either directly or indirectly, e.g., via measuring distance between the base and the movable arm at a pre-determined location. For instance, the calibrator can comprise a distance sensor disposed in one or both of the base and the movable arm.

The cell counter in this aspect may include a sample mounting system that comprises a height adjustment pin in one of the base or the movable arm. The sample mounting system can also include a height adjustment pin receiver in the other of the base or the movable arm. The height adjustment pin can be connected to an actuator. In one embodiment, the height adjustment pin is a precision screw and the actuator is a motor.

In certain embodiments wherein the above-described cell counter comprises a height adjustment pin and a height adjustment pin receiver, the cell counter may also comprise a detector for detecting contact between the height adjustment pin and the height adjustment pin receiver. In particular embodiments, the detector accomplishes this by detecting completion of an electrical circuit formed by the contact between the height adjustment pin and the height adjustment pin receiver. In certain embodiments, contact between the height adjustment pin and the height adjustment pin receiver is made when the upper sample surface is in direct contact with the lower sample surface in the absence of a sample.

An eighth aspect features a method of counting cells comprising: (a) providing a cell counter as described in the seventh aspect above; (b) loading a sample onto the lower sample surface of the cell counter; (c) before, after, or simultaneously with step (b), moving the movable arm to a closed position relative to the base; (d) illuminating the sample via the bright-field light source, the fluorescence excitation source (when present), or a combination thereof (when the fluorescence excitation source is present); and (e) detecting and counting cells via the imaging system to produce cell count data. The method can further comprise, after step (c) the step of adjusting a distance between the base and the movable arm via the height adjustment pin.

In various embodiments, the step of moving the movable arm and/or adjusting the distance between the base and the movable arm is/are automated.

The method can also comprise the further steps of: (f) adjusting the amount of sample on the lower sample surface based on the cell count data; and (g) repeating steps (d) and (e).

In some embodiments, the method is practiced using a cell counter comprising a height adjustment pin in one of the base or the movable arm, which cell counter may also include a height adjustment pin receiver in the other of the base or the movable arm.

In certain embodiments, the method comprises setting a zero gap measurement by determining the distance between a point on the movable arm and a point on the base when the upper sample surface and the lower sample surface are in direct contact. In particular embodiments wherein the cell counter includes a height adjustment pin and a height adjustment pin receiver, this can be accomplished by (1) placing the upper sample surface in direct contact with the lower sample surface in the absence of a sample, (2) moving the height adjustment pin into contact with the height adjustment pin receiver, and (3) detecting the contact between the height adjustment pin and the height adjustment pin receiver when the upper sample surface is in direct contact with the lower sample surface in the absence of a sample. In particular embodiments, the contact between the height adjustment pin and the height adjustment pin receiver completes a circuit and the detection comprises detecting the completion of the circuit. Alternatively, the contact between the height adjustment pin and the height adjustment pin receiver can be detected by a distance sensor.

Other features and advantages of the invention will become apparent to those skilled in the art upon reference to the drawings and detailed description that follow.

DETAILED DESCRIPTION

Figure 1A:
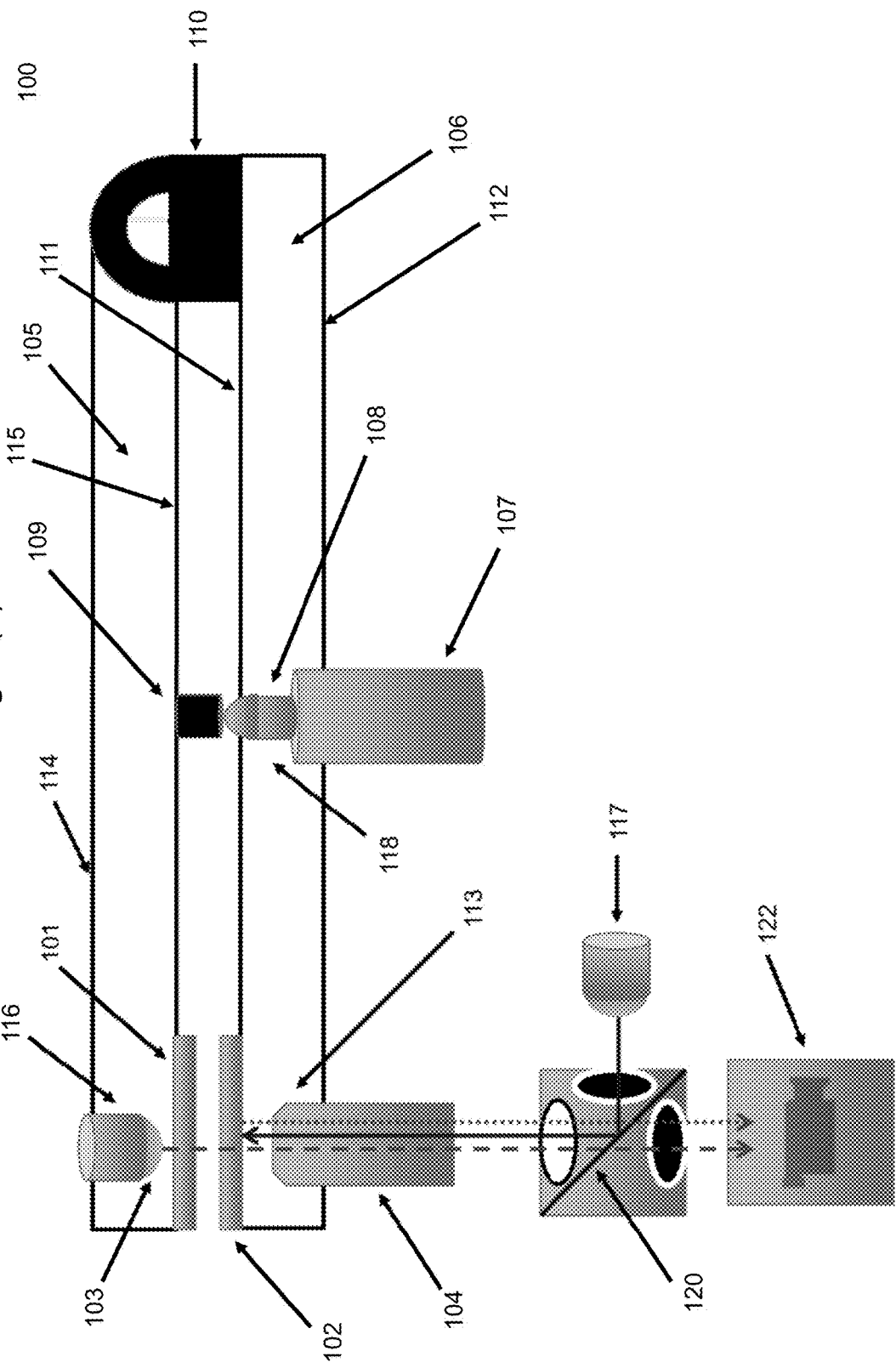
FIG. 1(a) depicts a close-up view of one embodiment of a sample mounting system.

The disclosures herein will be described more fully hereinafter with reference to the accompanying drawings, in which some, but not all possible embodiments are shown. Indeed, disclosures may be embodied in many different forms and should not be construed as limited to the embodiments set forth herein; rather, these embodiments are provided so that this disclosure will satisfy applicable legal requirements.

Many modifications and other embodiments disclosed herein will come to mind to one skilled in the art to which the disclosed devices, systems, and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. Although specific terms are employed herein, they are used in a generic and descriptive sense only and not for purposes of limitation.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the present disclosure be limited to the specific values recited when defining a range.

It is also to be understood that the terminology used herein is for the purpose of describing particular aspects only and is not intended to be limiting. As used in the specification and in the claims, the term "comprising" is to be interpreted as specifying the presence of the stated features, integers, steps, or components as referred to, but does not preclude the presence or addition of one or more features, integers, steps, or components, or groups thereof. Additionally, the term "comprising" is intended to include embodiments encompassed by the terms "consisting essentially of" and "consisting of." Similarly, the term "consisting essentially of" is intended to include embodiments encompassed by the term "consisting of."

Unless defined otherwise, all technical and scientific terms used herein have the same meaning as commonly understood by one of ordinary skill in the art to which the disclosed compositions and methods belong. In this specification and in the claims which follow, reference will be made to a number of terms which shall be defined herein.

The aforementioned problems are solved by the presently disclosed cell counter, which utilizes a reusable sample surface for efficient and cost-effective sample analysis instead of disposable cartridges. Thus the device reduces the total cost of ownership for the user through the elimination of the need to buy replacement cartridges.

Figure 1B:
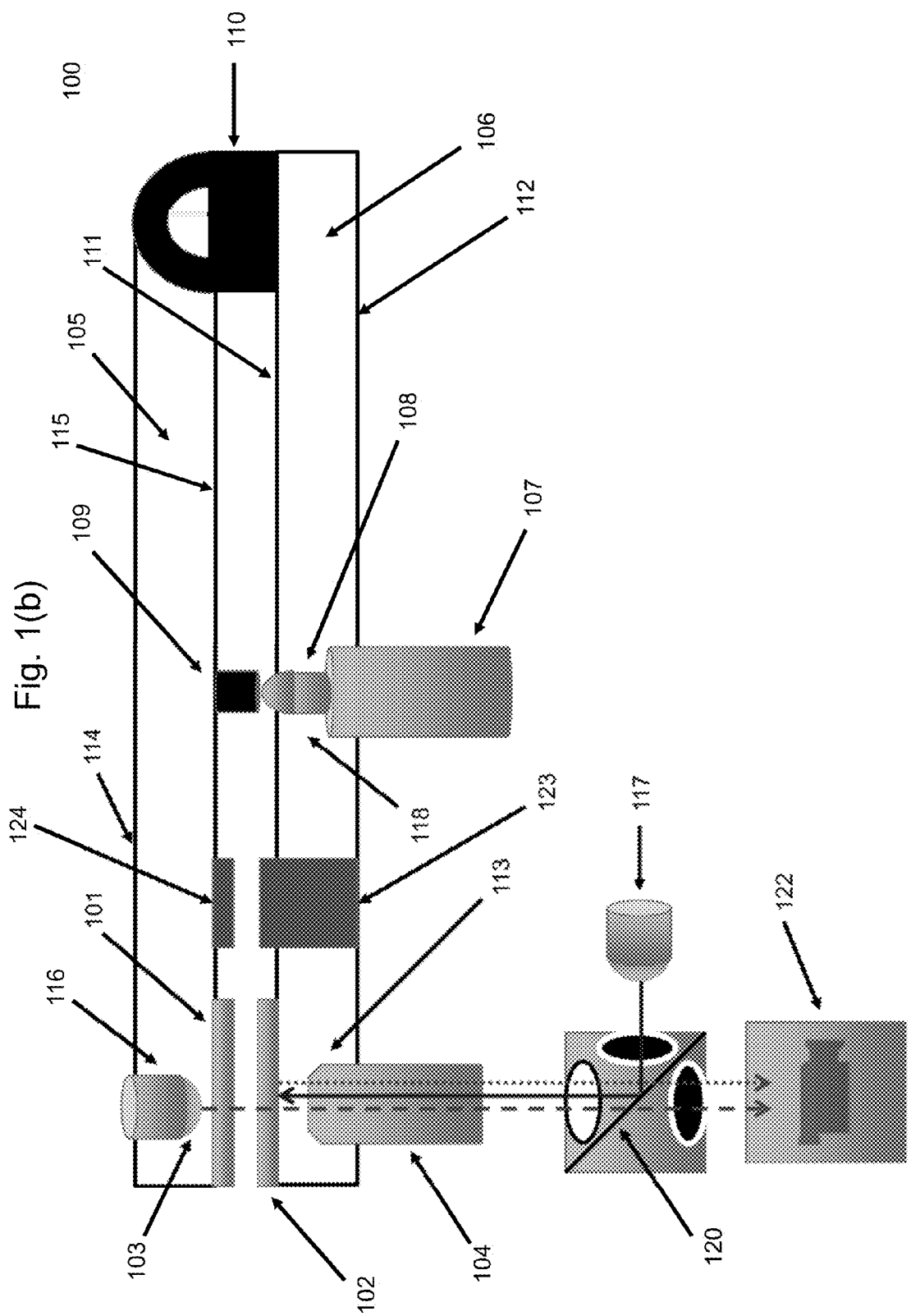
FIG. 1(b) depicts an alternative embodiment of the close-up view of the sample mounting system depicted in FIG. 1(a).

The present cell counter comprises a bright-field light source, a fluorescence excitation source, an imaging system, and a sample mounting system. Referring to FIGS. 1(a), 1(b) and/or 1(c), a cell counter of the present disclosure comprises a bright-field light source 103, which can be any type of bright-field light source as is found in bright-field microscopy. For example, the bright-field light source 103 can be any type of light emitting diode (LED). In other embodiments, the bright-field light source 103 can be any type of lamp, e.g., incandescent, halogen, or xenon lamps.

Bright-field light intensity can be varied as needed by the user, with intensity being analog controlled or digital controlled via, e.g., a computer.

Some embodiments of the cell counter can also utilize a diffusion screen and/or a condenser lens in between the bright-field light source 103 and the target sample.

Typically, the bright-field light source 103 is incorporated in the cover of the sample mounting system. However, it is possible for the bright-field light source 103 to be mounted in any way provided that light from the bright-field light source 103 passes through a sample placed on the lower sample surface 102 when the movable arm 105 is in the closed position relative to the base 106. For example, the cover, or in specific embodiments, the movable arm 105 can contain a bright-field light cavity 116 that itself does not contain the bright-field light source 103 but instead acts a light path, for example as an empty cavity or through fiber optics, for light emitted from the bright-field light source 103 to the sample.

In some embodiments, the bright-field light source 103 is positioned at the movable arm top side 114 and is configured to emit light onto lower sample surface 102 when the movable arm 105 is in the closed position relative to the base 106.

Figure 2:
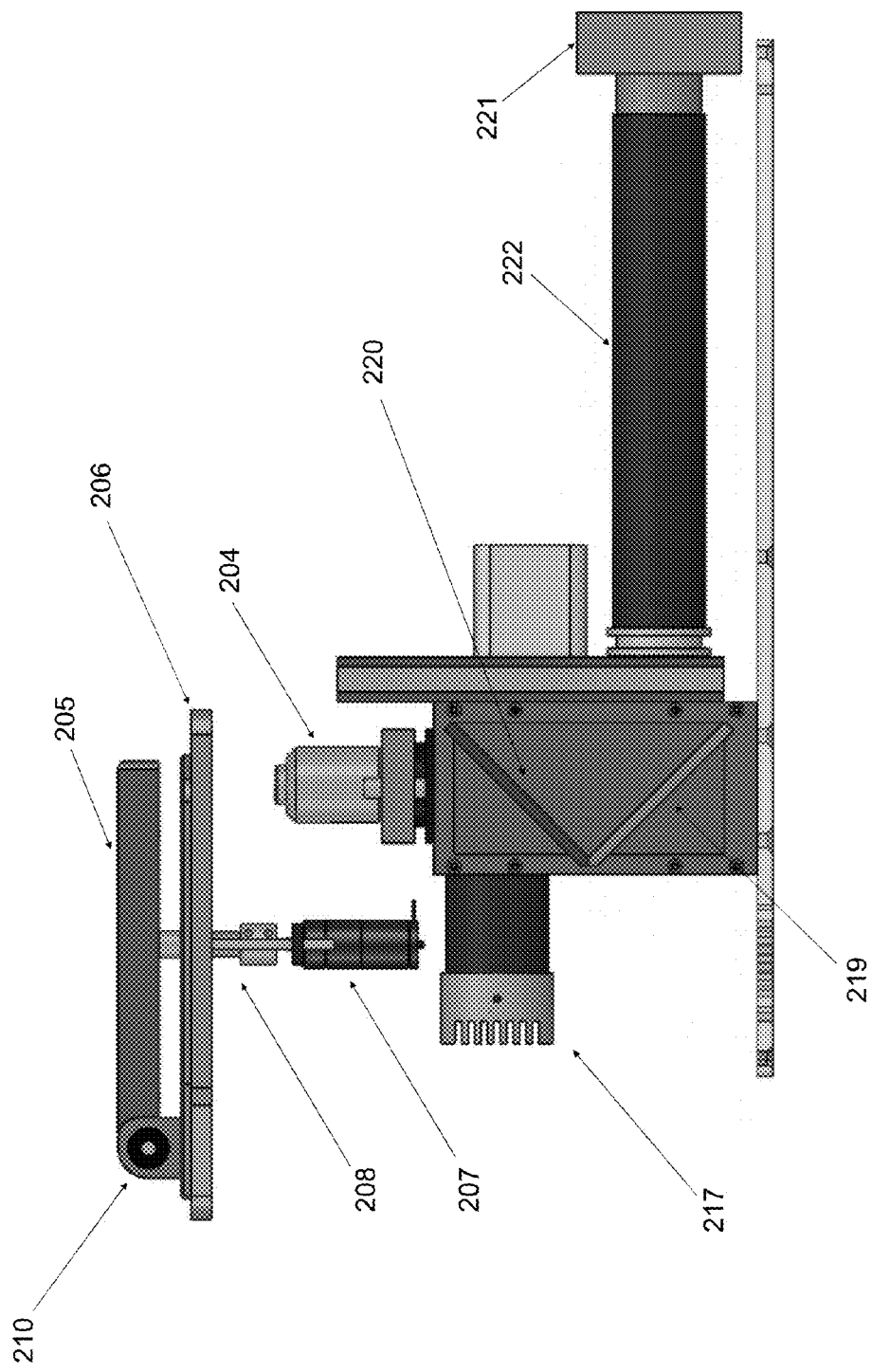
FIG. 2 depicts a side view, partially exposed, of an exemplary cell counter system.

Additionally, cell counters of the present disclosure optionally comprise a fluorescence excitation source in optical communication with the sample mounting system. Referring to FIG. 2, in some embodiments the fluorescence excitation source 217 is arranged in the cell counter in a position that places it in optical communication with a dichroic mirror 220 that is configured such that the dichroic mirror 220 reflects fluorescence excitation light emitted from the fluorescence excitation source towards a sample on the lower sample surface. Such a dichroic mirror in turn transmits any fluorescence emission light originating from the sample towards the imaging system 222.

It is also possible to orient the fluorescence excitation source and the dichroic mirror in such a manner that the dichroic mirror functions opposite as described above. That is, in such an embodiment, the dichroic mirror would transmit fluorescence excitation light from the fluorescence excitation source to a sample on the lower sample surface and would reflect fluorescence emission light originating from the sample towards the imaging system.

Some embodiments of the cell counter forego the need for a dichroic mirror by orienting the fluorescence excitation source in such a way that it is in direct optical communication with a sample on the lower sample surface. For example, referring to FIGS. 1(*a*), 1(*b*) and/or 1(*c*), the fluorescence excitation source can be configured such that excitation light from the fluorescence excitation source utilizes a gap in the objective lens cavity 113, thus bypassing the need for a dichroic mirror. The fluorescence excitation source can also be placed above or to the side of the lower sample surface 102 such that the sample receives excitation light from the fluorescence excitation source.

Suitable fluorescence excitation sources for use in the present cell counters include laser diodes and LEDs.

Referring to FIG. 2, mounted below the base 206 is an objective lens 204. Typically, after light from the bright-field light source passes through a sample on the lower sample surface, the light subsequently passes through the objective lens 204. The objective lens 204 is responsible for primary image formation and is involved in determining quality of images that the imaging system 222 is capable of producing. Objective lens 204 is also involved in determining the magnification of a particular sample and the resolution under which fine sample detail can be observed in the imaging system 222.

The objective lens 204 can be any objective lens as is typically used in bright-field or fluorescence microscopy.

The objective lens 204 is typically disposed below the base 206 in a position in alignment with the objective lens cavity of the base 206. Further, when the movable arm 205 is in the closed position, the bright-field light source will also be in alignment with the objective lens cavity and hence the objective lens creating an optical path that runs from the bright-field light source through the upper sample surface, the sample, the lower sample surface, the objective lens cavity, and then through the objective lens towards the imaging system.

The objective lens 204 is also in optical communication with fluorescence emission light from a fluorescently excited sample when a suitable light source is present. As arranged in FIG. 2, the objective lens 204 is also in optical communication with fluorescence excitation light from the fluorescence excitation source 217 after such light has been reflected by the dichroic mirror 220. As discussed above, however, in some embodiments, the fluorescence excitation source does not require use of a dichroic mirror, and thus in some cases the objective lens will not be in optical communication with the fluorescence emission light.

The distance between the objective lens 204 and the sample is typically, but not limited to, 10-20 mm, e.g., 10, 11, 12, 13, 14, 15, 16, 17, 18, 19, or 20 mm. Smaller or larger distances can be utilized, however, For example, 1, 2, 3, 4, 5, 6, 7, 8, or 9 mm between the objective lens 204 and the sample, or 21, 22, 23, 24, 25, 26, 27, 28, 29, 30, 31, 32, 33, 34, 35, 36, 37, 38, 39, 40, 45, 50, 55, 60 mm or more between the objective lens 204 and the sample.

An emission filter 219 can be mounted on a filter wheel containing at least one other emission filter. In some embodiments, the filter wheel can contain 2, 3, 4, 5, 6, 7, 8, 9 or more emission filters. The appropriate filter can be selected depending on the desired fluorescence wavelength. For example, an emission filter can be in any range of emitted fluorescent light, such as 460 nm (blue fluorescent protein), 479 nm (cyan fluorescent protein), 510 nm (wild type green fluorescent protein), 525 nm (green fluorescent protein), 530 nm (fluorescein isothiocyanate), 535 nm (yellow fluorescent protein), 620 nm (tetramethylrhodamine isothiocyanate/cyanine), or 630 nm (Texas Red). When the emission filter 219 is present, the excitation source (fluorescence excitation source 217) will excite the target fluorophore excitation wavelength(s), and in some embodiments all possible fluorophores simultaneously, while the selected emission filter 219 will transmit only the signal from the fluorophore(s) of interest to the imaging system 222.

In some aspects, the imaging system 222 comprises a detection device 221. The detection device 221 can be a camera, for example a CCD camera, a CMOS camera, a video camera, or a known photodetector, or the like, any of which may include a thermoelectric cooling capacity.

The imaging system utilizes software that can scan an image to identify and count cells. It can also measure the diameter and/or area of individual cells, to allow for size discrimination. In general, the user will be interested in the total number of cells, ratio of live to dead cells, number of nucleated cells, number of cells which fall within a size range, and various permutations of the above.

The imaging system will take an image or multiple images of each sample.

Images may be captured at different fluorescence wavelengths as required by the user.

The cell counter can also be run in a bright-field only mode to capture images of unstained cells (i.e., the bright field image).

Machine-readable storage media that can be used in conjunction with the imaging system include electronic, magnetic and/or optical storage media, such as magnetic floppy disks and hard disks; a DVD drive, a CD drive that in some embodiments can employ DVD disks; any of CD-ROM disks (i.e., read-only optical storage disks), CD-R disks (i.e., write-once, read-many optical storage disks), and CD-RW disks (i.e., rewriteable optical storage disks); a Blu-ray drive that can employ Blu-ray disks along with any of the aforementioned formats; and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, Blu-ray drive, or Compact Flash/PCMCIA/SD adapter) that accommodate and read from and/or write to the storage media. As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest.

Referring to FIGS. 1(a), 1(b) and/or 1(c), in some embodiments the sample mounting system 100 comprises a base 106 having a base top side 111, a base bottom side 112, and an objective lens cavity 113 configured to align with an objective lens 104 of the imaging system 122; a hinge 110 fixed to the base 106; a movable arm 105 fixed to the hinge 110, said movable arm 105 having a movable arm top side 114, a movable arm bottom side 115, and a bright-field light source cavity 116 near a proximal end of the movable arm configured to receive the bright-field light source 103; a lower sample surface 102 mounted to the base top side 111 in a position configured to receive bright-field light (indicated by dashed, downward-arrowed line) from the bright-field light source 102 when the movable arm 105 is in the closed position and to receive fluorescence excitation light from the fluorescence excitation source 117 (with fluorescent light in some embodiments reflected by a dichroic mirror 120), when the fluorescence excitation source is present; and an upper sample surface 101 mounted to the movable arm bottom side 115 of the movable arm 105 in a position configured to receive fluorescent light from the fluorescence excitation source (fluorescence excitation light indicated by solid, upward-arrowed line; fluorescence emission light indicated by dotted, downward-arrowed line) when the movable arm 105 is in the closed position, when the fluorescence excitation source is present, and to receive bright-field light from the bright field light source 103.

In some aspects, the base 106 further comprises an adjustment pin hole 118 through the base top side 111 to the base bottom side 112 configured to receive a height adjustment pin 108. In such aspects, the movable arm 105 can further comprise, when the base bottom side 106 is configured to receive a height adjustment pin 108, a height adjustment pin receiver 109 fixed to the movable arm bottom side 115 in a position aligned with the adjustment pin hole 118 when the movable arm 105 is in a closed position.

In embodiments where the base 106 comprises an adjustment pin hole 118, the cell counter further comprises a height adjustment pin 108 mounted to the base 106 through the adjustment pin hole 118. The height adjustment pin 108 when present is connected to an actuator 107 that is configured to either manually or automatically adjust the height of the height adjustment pin 107. In some embodiments, the height adjustment pin 108 is a precision screw and the actuator 107 is a motor. In such embodiments, the motor moves precision screw up and down within the adjustment pin hole 118. In specific embodiments, the motor is designed to produce rotational motion of precision screw, which bears against a height adjustment pin receiver 109 extending from the movable arm 105 into the adjustment pin hole 118. As driven by the motor, the rotation of precision screw against height adjustment pin receiver 109 causes the controlled translation of the movable arm 105, and consequently, the upper sample surface 101 that is housed thereon.

In one embodiment, the motor has an encoder that automatically moves precision screw up and down to a predetermined position. However, the motor can be any motor, linear actuator or linear translator motor.

To position the movable arm 105 into a measurement position, the actuator 107 moves the adjustment pin 108, which in turn moves the adjustment pin receiver 109, which in turn moves the movable arm 105, thereby controlling the distance between the upper sample surface 101 and the lower sample surface 102. In one embodiment, the actuator 107 moves the adjustment pin 108 down, bringing movable arm 105 closer to base 106 and reducing the distance between the upper sample surface 101 and the lower sample surface 102. Data regarding the observed optical properties is transmitted to the imaging system 122, which can perform a variety of calculations based on the measured optical properties.

The hinge 110 can be positioned on the base 106 so that the movable arm 105 can move from an open position to a closed position relative to the base 106. In some aspects, the hinge 110 position is distal on the base 106 relative to the objective lens cavity 113.

The movable arm can further comprise a calibration means (also termed "calibrator" herein). The movable arm may be calibrated by establishing a known location along the path of travel. This may be accomplished in a multitude of ways, including but not limited to:

A) A known gap may be established through use of a calibrated mechanical spacer or gap tool.

Figure 1C:
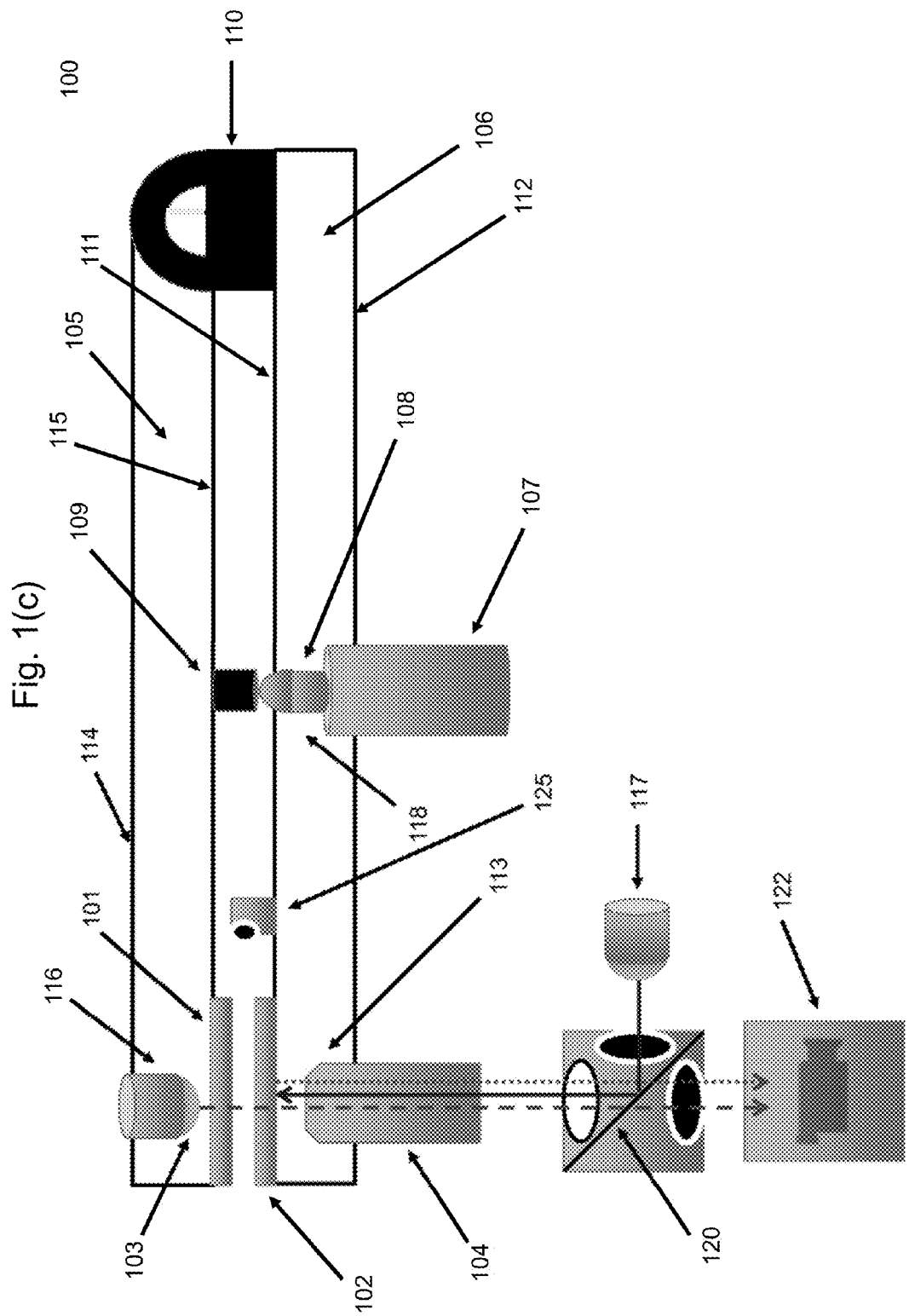
FIG. 1(c) depicts another alternative embodiment of the close-up view of the sample mounting system depicted in FIG. 1(a).

B) Referring to FIG. 1(c), a camera 125 or other imaging device may be used to view the edges of the upper sample surface 101 and lower sample surface 102. The gap can then be adjusted until the image system 122 confirms the spacing is correct.

C) A magnet, or electro-magnet, may provide resistance to the motor in its bottom-most position. When the motor successfully lifts the arm from this resting position, the exact motor position at the shortest path is established.

D) Optical calibration using markers etched on the optical surfaces themselves and visualized by the imaging system.

E) The motor may establish a fixed or "home" position by encountering a mechanical stop positioned at a set reference location.

In certain embodiments, the gap may be set or calibrated by reference to a "zero gap" or "P-zero", i.e., a measurement of zero when the upper sample surface 101 is in contact with the lower sample surface 102 in the absence of a sample. To accomplish this, the adjustment pin 108 is lowered such that it is not in contact with the adjustment pin receiver 109; then the movable arm 105 is positioned such that the upper sample surface 101 rests directly on the lower sample surface 102. The adjustment pin 108 is raised until it makes contact with the adjustment pin receiver 109, the contact is detected and the "zero gap" measurement is set.

The initiation of contact between the adjustment pin 108 and the adjustment pin receiver 109 can be detected in a variety of ways, including through the use of various types of proximity sensors or pressure pads. In a preferred embodiment, the initiation of contact is detected electrically, via completion of a circuit. In this embodiment, the adjustment pin 108 and the adjustment pin receiver 109 are connected directly or indirectly to a voltage source. The circuit is completed when the adjustment pin 108 and the adjustment pin receiver 109 contact one another, an event that is detectable by any common means known in the art. This method has the advantage of being self-correcting under varying conditions. That is, the "zero gap" measurement can be reliably made each time the instrument is used, even if the relationship between the adjustment pin 108 and the adjustment pin receiver 109 changes over time, such as might occur by moving the instrument or by normal wear and tear on these elements.

In one embodiment, the gap or spacing between the upper sample surface 101 and the lower sample surface 102 can be calibrated using a capacitive displacement sensor system. Such systems are well known in the art. See, e.g., Capacitive Sensor Operation and Optimization; Capacitive Sensor TechNote LT03-0020, Lion Precision, Oakdale, Minn.; URL lionprecision.com). Such devices are composed of two conductive components, typically referred to as a sensor and a target. In application to the present instrument, one of the components is placed on the movable arm, while the other component is placed in a location on the base, such that when the movable arm is in position to be lowered, the two components are aligned with one another. The capacitive displacement sensor can be located at any position on the movable arm/base relative to the adjustment pin and adjustment pin receiver. In an embodiment shown in FIG. 1(b), the capacitive displacement sensor 123/124 is located between the adjustment pin/adjustment pin receiver 108/109 and the upper/lower samples surfaces 101/102. In FIG. 1(b), the probe component 123 of the sensor is fitted into base 106 and the target component 124 is placed in movable arm 105.

As the skilled person will understand, the capacitive displacement sensor system can also be used to generate a "zero gap" measurement as discussed above. This can be done simply by taking the measurement between the movable arm 105 and base 106 when the upper and lower sample surfaces 101/102 are in contact without a sample. Alternatively, the sensor can detect and note a movement between the upper and lower sample surfaces 101/102, i.e., when they are moved apart from one another. These techniques can be utilized in embodiments of the cell counter that do not comprise a height adjustment pin or height adjustment pin receiver.

The skilled person will understand that other distance sensors can be used in place of the capacitive displacement sensor for calibration and/or setting of a zero gap measurement. For instance, time of flight sensors based on light or ultrasound can be used.

While the upper sample surface 101 and the lower sample 102 surface are not disposable cartridges, that does not mean that these sample surfaces cannot be removed from the sample mounting system for, e.g., cleaning, repair, replacement, etc. It is possible, however, to permanently affix one or both of the sample surfaces to their respective base or cover if so desired.

The upper and lower sample surfaces can comprise any transparent or translucent materials including, but not limited to, glass, fused silica, sapphire, quartz or optical grade plastics. The upper sample surface and the lower sample surface can comprise the same material, or they can comprise different materials from each other.

Figure 3:
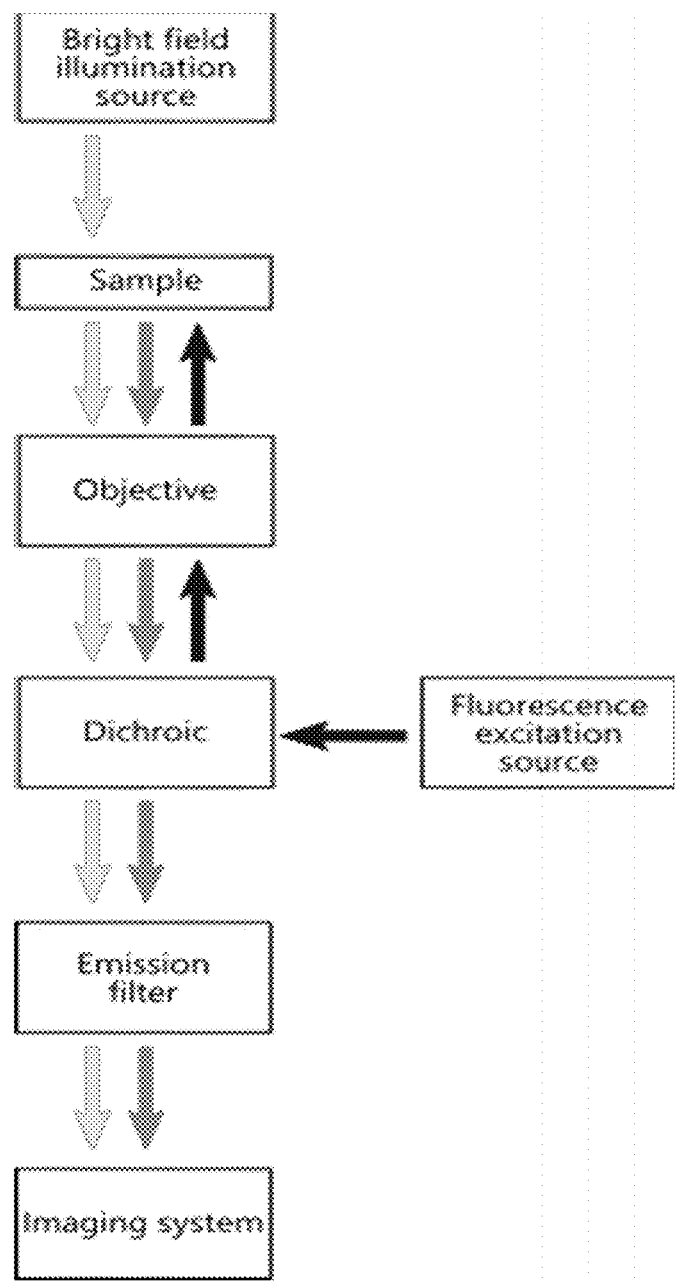
FIG. 3 illustrates an exemplary orientation of a cell counter of the present disclosure.

FIG. 3 shows one possible layout for the present cell counter. This design couples a fluorescence excitation source to the imaging path via a dichroic mirror. This dichroic mirror reflects the excitation light and transmits the emitted fluorescence. In bright-field imaging mode, the light from the bright-field light source (downward light gray arrows) is transmitted through the sample, the objective lens and the dichroic mirror to the imaging system.

In fluorescence imaging mode, the fluorescence excitation light (upward arrows) is reflected by the dichroic mirror through the objective to the sample. The fluorescence emitted by the sample (downward dark gray arrows) is transmitted through the objective lens, the dichroic mirror, and the emission filter.

Figure 4:
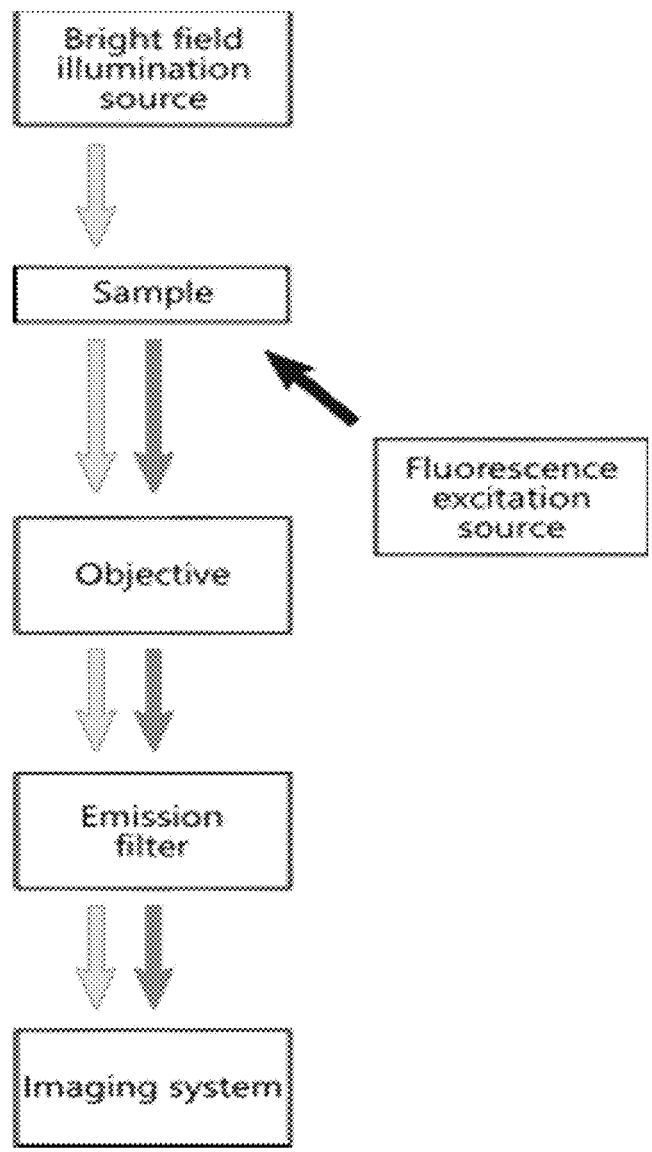
FIG. 4 illustrates another exemplary orientation of a cell counter of the present disclosure.
Figure 5:
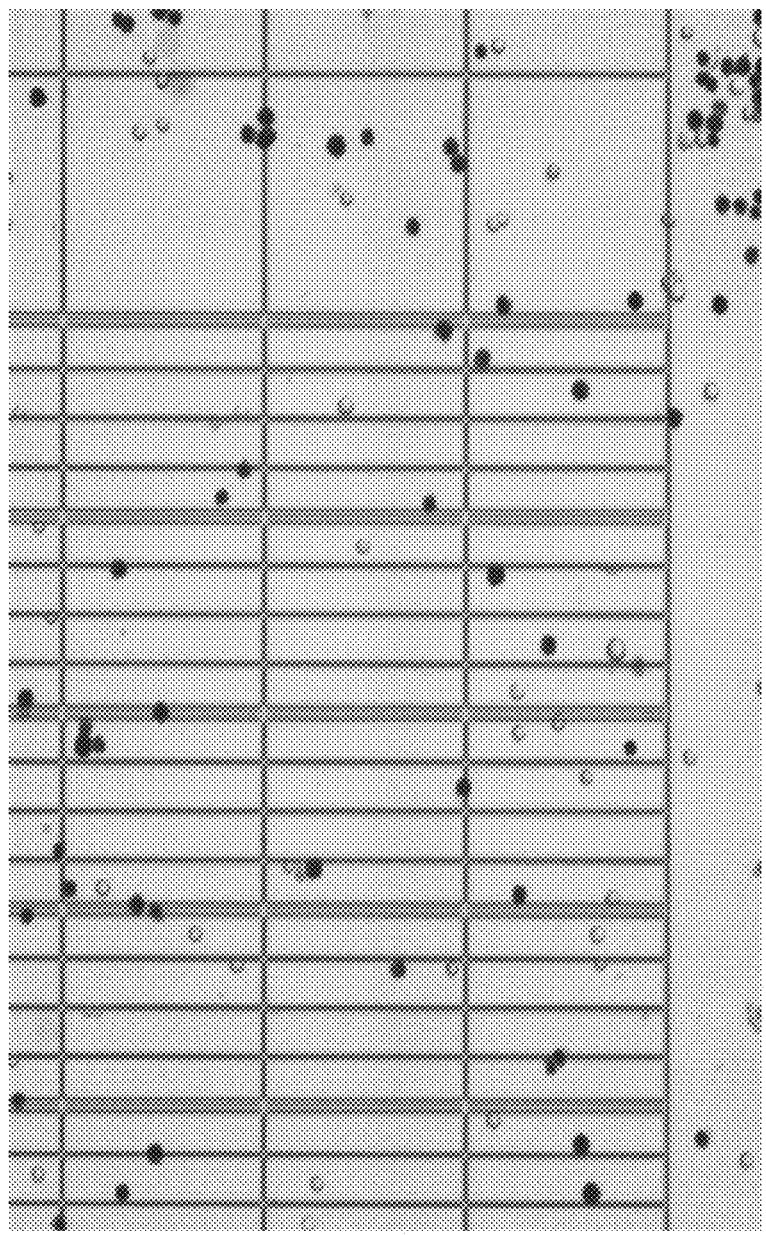
FIG. 5 shows an exemplary bright-field image from a cell counter of the present disclosure.

FIG. 4 shows a design for the cell counter where the fluorescence excitation source is decoupled from the imaging path. An advantage of such a design is that the illumination and imaging paths are separate and can be adjusted independently. There is also no dichroic mirror, which simplifies and shortens the imaging path.

Operation of the cell counters disclosed herein can take place through a variety of methods. For example, cell counting can be effectuated through loading a sample onto the lower sample surface of the cell counter; moving the movable arm to a closed position relative to the base; illuminating the sample via the bright-field light source, the fluorescence excitation source (when present), or a combination thereof (when the fluorescence excitation source is present); and detecting and counting cells via the imaging system. Any of these operation steps can be repeated as needed.

In preparing samples for counting utilizing the presently disclosed apparatus, cells from an adherent cell culture or a suspension can be re-suspended in a buffer and combined with a fluorescent and/or non-fluorescent dye at a known concentration. Once labeled, the sample can be aspirated with a pipette and loaded onto the lower sample surface.

Note that the sample loading and moving the cover/arm steps can be performed in any order relative to each other. Thus, it is possible to load a sample onto the lower sample surface before, after, or simultaneous with the moving the arm into the closed position. No matter what the timing between the steps, the end result will be that liquid samples will be sandwiched between the upper sample surface and the lower sample surface prior to sample analysis.

Movement of the cover (or in some embodiments the arm) between open and closed positions can be accomplished either manually or automatically. Referring to FIGS. 1(a), 1(b) and/or 1(c), the hinge 110 permits movement of the movable arm 105 from a fully closed position where the upper sample surface 101 and the lower sample surface 102 are in contact or at their closest position relative to one another. In moving to a fully open position, which can be 180° or more relative to the fully closed position, the movable arm 105 can be placed in locked positions in between the fully closed position and the fully open position using mechanical or electronic mechanisms if desired. It is also possible for the movable arm 105 to not have any lockable positions in between the fully open position and the fully closed position.

When using a presently disclosed cell counter, a droplet from a liquid sample is placed on the lower sample surface. As discussed above, the movable arm can be first moved out of the way, either manually or automatically, before depositing such a sample, or the movable arm can already be in the closed position or on its way to the closed position when the sample is deposited on the lower sample surface. Volume placed on the lower sample surface can vary, with typical sample volumes of less than 1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 91, 91, 92, 93, 94, 95, 96, 97, 98, 99, 100 µl or greater, or any value in between.

The movable arm will then be moved back above the sample. If the cell counter utilizes an adjustment pin, the actuator will position the upper sample surface a precise distance above the lower sample surface trapping a volume of liquid between the two. The distance or gap between the two surfaces will be predetermined dependent on the volume added by the user, with typical gaps being, e.g., less than 25, 25, 30, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 µm or greater, or any value in between.

By using larger or smaller sample volumes and adjusting the height of the path to evenly distribute the sample over the surface, an increase the dynamic range of cell densities that can be counted. If a sample has a very high density of cells, the user could add a lower volume of the sample liquid such as 2 µl to the lower sample surface in which case the movable arm would move to the lowest possible setting to evenly spread the smaller sample volume. In the opposing case, a user with a low cell density could add a larger volume, up to e.g. 100 µl, to the lower sample surface increasing the total number of cells yielding a more accurate result.

In some embodiments, dyes can be added to the sample. Exemplary fluorescent dyes for use in the present cell counter include, but are not limited to, acridine orange (AO), propidium iodide (PI), and Green Fluorescent Protein (GFP). Other possible dyes include ethidium bromide, Red Fluorescent Protein, 4',6-Diamidino-2-phenylindole (DAPI), Hoescht (33342, 33258, 34580), calcein, fluorescein isothiocyanate (FITC), fluorescein diacetate (FDA), and allophylcocyanin, but any fluorescent dye used for cell detection is compatible with the present cell counters.

AO is a fluorescent dye or stain which preferentially binds to nucleic acids (DNA and RNA) in live cells. PI is a fluorescent nucleic acid binding vital dye that is actively excluded by live cells, while dead cells will take up the dye. AO and PI can be used in tandem to obtain a count of viable nucleated cells within a total population. When using this assay two fluorescence microscopy images can be taken, one using the emission filter for AO and the other using the emission filter for PI. These can then be superimposed for a final count of live and dead cells.

GFP is a fluorescent marker protein that has been artificially incorporated into a cells genome and will fluoresce when a gene of interest is activated within a cell. In this assay, a count of fluorescent cells under certain conditions could be compared to controls or cells under different conditions.

Non-fluorescent dyes including, but not limited to, trypan blue or erythrosin B, can be utilized for bright-field images produced by the cell counter. Trypan blue is a vital dye that is actively excluded by live cells, while dead cells will take up the dye. This dye is used in bright field microscopy to discriminate between live and dead cells within a population and obtain a count of for the number of viable (non-stained) cells versus dead (stained) cells. Erythosin B (also known as ethyrosine or Red No. 3) is a vital dye that is actively excluded by live cells, while dead cells will take up the dye.

The present invention is not limited to the embodiments described and exemplified herein. It is capable of variation and modification within the scope of the appended claims.

We claim:

1. A cell counter comprising:
   (i) a bright-field light source;
   (ii) an imaging system; and
   (iii) a sample mounting system comprising upper and lower sample surfaces configured for direct receipt of a cell suspension for counting, the system comprising:
   (A) a base having a base top side, a base bottom side, and an objective lens cavity located on the base so as to align with and receive an objective lens of the imaging system;
   (B) a hinge fixed to the base;
   (C) a movable arm fixed to the hinge, said movable arm having a movable arm top side, a movable arm bottom side, and a bright-field light source cavity located on a portion of the movable arm distal to the hinge and configured to receive the bright-field light source;
   (D) the lower sample surface mounted to the base top side in a position configured to receive bright-field light from the bright-field light source when the movable arm is in a closed position; and
   (E) the upper sample surface mounted to the movable arm bottom side of the movable arm in a position configured to receive bright-field light from the bright field light source;
   wherein a distance between the lower sample surface and the upper sample surface when the moveable arm is in the closed position is adjustable to accommodate variable volumes of cell suspension samples deposited between the upper and lower sample surfaces;

wherein the system is re-usable by moving the movable arm to an open position and cleaning the sample surfaces.

2. The cell counter of claim 1, further comprising a fluorescence excitation source; wherein the lower sample surface is configured to receive fluorescent light from the fluorescence excitation source and/or the upper sample surface is configured to receive fluorescent light from the fluorescence excitation source when the movable arm is in the closed position.

3. The cell counter of claim 1, wherein the sample mounting system comprises a calibrator for detecting and/or calibrating distance between the lower sample surface and the upper sample surface.

4. The cell counter of claim 3, wherein the calibrator comprises a distance sensor disposed in one or both of the base and the movable arm.

5. The cell counter of claim 1, wherein the sample mounting system comprises a height adjustment pin in one of the base or the movable arm and a height adjustment pin receiver in the other of the base or the movable arm and the distance between the lower sample surface and the upper sample surface is adjustable via the height adjustment pin.

6. The cell counter of claim 5, comprising a detector for detecting contact between the height adjustment pin and the height adjustment pin receiver.

7. The cell counter of claim 6, wherein the detector detects completion of an electrical circuit formed by the contact between the height adjustment pin and the height adjustment pin receiver.

8. The cell counter of claim 7, wherein the contact between the height adjustment pin and the height adjustment pin receiver is made when the upper sample surface is in direct contact with the lower sample surface in the absence of a sample.

9. The cell counter of claim 5, wherein the height adjustment pin is connected to an actuator.

10. The cell counter of claim 9, wherein the height adjustment pin is a precision screw and the actuator is a motor.

11. A method of counting cells comprising:
(a) providing a cell counter comprising:
(i) a bright-field light source;
(ii) an optional fluorescence excitation source;
(iii) an imaging system; and
(iv) a sample mounting system comprising:
(A) a base having a base top side, a base bottom side, and an objective lens cavity located on the base so as to align with and receive an objective lens of the imaging system; and
(B) a hinge fixed to the base;
(C) a movable arm fixed to the hinge, said movable arm having a movable arm top side, a movable arm bottom side, and a bright-field light source cavity located on a portion of the movable arm distal to the hinge and configured to receive the bright-field light source;
(D) a lower sample surface mounted to the base top side in a position configured to receive bright-field light from the bright-field light source when the movable arm is in a closed position; and
(E) an upper sample surface mounted to the movable arm bottom side of the movable arm in a position configured to receive bright-field light from the bright field light source;
wherein a distance between the lower sample surface and the upper sample surface when the movable arm is in the closed position is adjustable to accommodate variable volumes of liquid sample deposited between the upper and lower sample surfaces;
(b) loading a cell suspension sample of known volume onto the lower sample surface;
(c) before, after, or simultaneously with step (b), moving the movable arm to the closed position relative to the base;
(d) illuminating the sample via the bright-field light source, the fluorescence excitation source if present, or a combination thereof;
(e) detecting and counting cells via the imaging system to produce cell count data;
(f) before, after or simultaneously with step (b), (c), (d) or (e), adjusting the distance between the lower sample surface and the upper sample surface to accommodate the volume of sample loaded onto the lower sample surface; and
(g) preparing the cell counter for repeating steps (b) (f) by moving the movable arm into an open position relative to the base and removing the cell suspension sample from the upper and lower sample surfaces.

12. The method of claim 11, wherein the moving step is automated.

13. The method of claim 11, wherein the sample mounting system comprises a height adjustment pin in one of the base or the movable arm and a height adjustment pin receiver in the other of the base or the movable arm and the distance between the lower sample surface and the upper sample surface is adjusted via the height adjustment pin.

14. The method of claim 13, wherein the height adjustment pin is connected to an actuator.

15. The method of claim 14, wherein the height adjustment pin is a precision screw and the actuator is a motor.

16. The method of claim 13, wherein the adjusting step is automated.

17. The method of claim 11, comprising the further steps of:
(h) adjusting the volume of sample on the lower sample surface based on the cell count data; and
(i) repeating steps (b) through (g).

18. The method of claim 11, further comprising setting a zero gap measurement by determining a distance between a point on the movable arm and a point on the base when the upper sample surface and the lower sample surface are in direct contact in the absence of a sample.

19. The method of claim 18, wherein the cell counter comprises a height adjustment pin in one of the base or the movable arm and a height adjustment pin receiver in the other of the base or the movable arm, and the method comprises setting the zero gap measurement by (1) placing the upper sample surface in direct contact with the lower sample surface in the absence of a sample, (2) moving the height adjustment pin into contact with the height adjustment pin receiver, and (3) detecting the contact between the height adjustment pin and the height adjustment pin receiver when the upper sample surface is in direct contact with the lower sample surface in the absence of a sample.

20. The method of claim 9, wherein the contact between the height adjustment pin and the height adjustment pin receiver completes a circuit and the detection comprises detecting the completion of the circuit.

21. The method of claim 19, wherein the contact between the height adjustment pin and the height adjustment pin receiver is detected by a distance sensor.

\* \* \* \* \*

UNITED STATES PATENT AND TRADEMARK OFFICE
CERTIFICATE OF CORRECTION

PATENT NO. : 10,302,568 B2
APPLICATION NO. : 15/628394
DATED : May 28, 2019
INVENTOR(S) : Kielhorn et al.

Page 1 of 1

It is certified that error appears in the above-identified patent and that said Letters Patent is hereby corrected as shown below:

On the Title Page

Item (72), Add the following inventor name: "Andrew William Jones, Hitchin, Hertfordshire (UK)".

Signed and Sealed this
Fifth Day of May, 2020

Andrei Iancu
*Director of the United States Patent and Trademark Office*